US005512329A

United States Patent [19]
Guire et al.

[11] Patent Number: 5,512,329
[45] Date of Patent: *Apr. 30, 1996

[54] SUBSTRATE SURFACE PREPARATION

[75] Inventors: Patrick E. Guire; Shawn G. Dunkirk, both of Eden Prairie; Mark W. Josephson, Richfield; Melvin J. Swanson, Carver, all of Minn.

[73] Assignee: BSI Corporation, Eden Prairie, Minn.

[*] Notice: The term of this patent shall not extend beyond the expiration date of Pat. No. 5,002,582.

[21] Appl. No.: 173,914

[22] Filed: Dec. 27, 1993

Related U.S. Application Data

[63] Continuation of Ser. No. 816,771, Jan. 2, 1992, abandoned, which is a continuation of Ser. No. 675,604, Mar. 25, 1991, abandoned, which is a division of Ser. No. 447,802, Dec. 8, 1989, Pat. No. 5,002,582, which is a division of Ser. No. 223,149, Jul. 22, 1988, abandoned, which is a continuation-in-part of Ser. No. 138,226, Dec. 24, 1987, abandoned, which is a continuation-in-part of Ser. No. 920,567, Oct. 17, 1986, abandoned, and Ser. No. 108,765, Oct. 15, 1987, Pat. No. 4,973,493, which is a continuation-in-part of Ser. No. 428,074, Sep. 29, 1982, Pat. No. 4,722,906.

[51] Int. Cl.$^6$ .............................. C08F 2/48; B05D 3/06; B05D 1/38
[52] U.S. Cl. ................... 427/508; 427/2.1; 427/2.28; 427/407.1; 427/553
[58] Field of Search ........................ 427/508, 515, 427/553, 2.1, 2.28, 407.1

[56] References Cited

U.S. PATENT DOCUMENTS

| | | |
|---|---|---|
| 3,131,060 | 4/1964 | Cassiers et al. . |
| 3,320,116 | 5/1967 | Tocker ................................ 428/483 |
| 3,807,999 | 4/1974 | DeSchrijver et al. .................. 96/27 F |
| 3,808,113 | 4/1974 | Okamura et al. . |
| 3,826,678 | 7/1974 | Hoffman et al. . |
| 3,888,833 | 6/1975 | Lednicer et al. . |
| 3,955,012 | 5/1976 | Okamura et al. . |
| 3,959,078 | 5/1976 | Guire .................................. 435/176 |
| 4,007,089 | 2/1977 | Smith, III ............................ 435/181 |
| 4,039,652 | 8/1977 | Adams et al. ........................ 424/1 |
| 4,160,698 | 7/1979 | Miyair et al. ........................ 435/173 |
| 4,233,402 | 4/1978 | Maggio et al. ...................... 435/7 |
| 4,240,163 | 12/1988 | Galin . |
| 4,273,873 | 6/1981 | Sugitach et al. . |
| 4,307,071 | 8/1981 | Murray et al. . |
| 4,309,453 | 1/1982 | Reiner et al. ........................ 427/553 |
| 4,311,573 | 1/1982 | Mayhan et al. . |
| 4,326,532 | 4/1982 | Hammer ............................. 128/349 R |
| 4,331,697 | 5/1982 | Kudo et al. ......................... 427/2 |
| 4,378,224 | 3/1983 | Nimni et al. . |
| 4,378,435 | 3/1983 | Takagi et al. . |
| 4,413,052 | 11/1983 | Green et al. ........................ 430/327 |
| 4,419,444 | 12/1983 | Quash . |
| 4,434,150 | 2/1984 | Azad et al. . |
| 4,451,568 | 5/1984 | Schneider et al. .................. 435/181 |
| 4,464,468 | 8/1984 | Avrameas et al. .................. 435/177 |
| 4,500,676 | 2/1985 | Balazs . |
| 4,526,714 | 7/1985 | Feijen et al. . |
| 4,526,909 | 7/1985 | Urist . |
| 4,530,974 | 7/1985 | Munro et al. . |
| 4,536,179 | 8/1985 | Anderson et al. . |
| 4,589,881 | 5/1986 | Pierschbacher . |
| 4,589,964 | 5/1986 | Mayhan et al. . |
| 4,595,632 | 6/1986 | Mayhan et al. . |
| 4,597,999 | 7/1986 | Lingwood . |
| 4,605,413 | 8/1986 | Urry et al. ......................... 623/11 |
| 4,657,820 | 4/1987 | Halpern et al. . |
| 4,663,163 | 5/1987 | Hou et al. ......................... 424/527 |
| 4,663,233 | 5/1987 | Beavers . |
| 4,678,808 | 8/1987 | Jarrett et al. . |
| 4,687,808 | 8/1987 | Jarrett et al. . |
| 4,715,858 | 12/1987 | Lindstrom . |
| 4,716,122 | 12/1987 | Scheefers . |
| 4,722,906 | 2/1988 | Guire . |
| 4,743,258 | 5/1988 | Ikada et al. ....................... 427/255.6 |
| 4,828,563 | 5/1989 | Muller-Lierheim .............. 623/16 |
| 4,833,093 | 5/1989 | Malmqvist et al. .............. 427/255.6 |
| 4,833,218 | 5/1989 | Lee ................................... 525/455 |
| 4,873,033 | 10/1989 | Heckmann et al. .............. 264/41 |
| 4,948,819 | 8/1990 | Green et al. ..................... 522/31 |
| 4,973,493 | 11/1990 | Guire ................................ 427/2 |
| 4,979,959 | 12/1990 | Guire ................................ 623/66 |
| 4,987,032 | 1/1991 | Miyasaka et al. ................ 427/55 |
| 5,002,582 | 3/1991 | Guire ................................ 623/66 |
| 5,002,883 | 3/1991 | Bieniarz et al. . |
| 5,128,170 | 7/1992 | Matsuda et al. .................. 427/2 |
| 5,154,808 | 10/1992 | Miyasaka et al. ................ 427/553 |
| 5,208,166 | 5/1993 | Saunders et al. ................ 427/338 |
| 5,217,492 | 6/1993 | Guire et al. ...................... 427/2 |
| 5,217,743 | 6/1993 | Farah ................................. 427/2 |

OTHER PUBLICATIONS

Derwent Abstract 48907 of European Patent 322557 A, General Electric, Jul. 1989.

Ebert, et al., "The Anticoagulant Activity of Derivatized and Immobilized Heparins", Eds., Am. Chem. Soc., (1982), pp. 161–176. (no month available).

Larsson, et al., "Covalent Binding of Proteins to Grafted Plastic Surfaces Suitable for Immunoassays", J. Immuno. Methods, (1987), pp. 129–135. no month available.

Engbers, et al., "An In Vitro Study of Adhesion of Blood Platelets Into Vascular Catheters", J. Biom. Mat., Res., vol. 21, (1987), pp. 613–627. (no month available).

Evangelista, et al., "Coating of Two Polyether–polyurethanes and Polyethylene with Heparin–poly (vinyl alcohol) Hydrogel", Biomaterials, vol. 7, May 1986, pp. 206–211.

Palatianos, et al., "Extracorporeal Left Ventricular Assistance with Prostacyclin and Heparinized Centrifugal Pump", The Annals of Thoracic Surgery, vol. 35, No. 5, (1983), pp. 504, 515 (May).

(List continued on next page.)

Primary Examiner—Diana Dudash
Attorney, Agent, or Firm—Philip M. Goldman; James R. Haller; Gregory P. Kaihoi

[57] ABSTRACT

Surfaces are provided with desired characteristics of a polymer by covalently bonding polymer molecules to the surface through external activation (e.g., actinic radiation) of latent reactive groups, such as photoactivatable ketones, carried by the polymer molecules. The initial surfaces are free of chemical groups added by surface pretreatment and which chemically participate in the covalent bonding process.

22 Claims, No Drawings

OTHER PUBLICATIONS

Larm, et al., "A New Non–Thrombogenic Surface Prepared by Selective Covalent Binding of Heparin Via a Modified Reducing Terminal Residue", Biomat. Med. Dev., Art. Org., 11 (2&3), (1983), pp. 161–173. no month available.

Hoffman, et al., "A New Method for Covalently Coupling of Heparin and Other Glycosaminoglycans to Substances Containing Primary Amino Groups", vol. 117, Carbohydrate Research, (1983), pp. 328–331. no month available.

Bennegard, et al., "Material Thrombogenicity in Central Venous Catheterization", Acta. Anaesth. Scand., (1982), vol. 26, pp. 112–120. (no month available).

Nilsson, et al., "Polarographic p°2 Sensors With Heparinized Membranes for In Vitro and Continuous In Vivo Registration", Scan. J. Clin. Lab. Invest., vol. 41, (1981), pp. 557–563. no month available.

Kim, et al., Surface Modification of Polymers for Improved Blood Compatibility, CRC Critical Reviews in Biocompatibility, vol. 1, Issue 3, pp. 229–260. no month available.

Guire, et al., *Glycoconjugate Research*, vol. II, (1979), pp. 1051–1054. no month available.

Guire, "Photochemical Immobilization of Enzymes and Other Biochemicals", Methods in Enzymology, vol. XLIV, (1976), pp. 280–288, (ed. Klaus Mosbach). no month available.

Guire, "Photochemical Coupling of Enzymes to Mammalian Cells", Pharmacological Research Communications, vol. 9, (1977), pp. 131–141. no month available.

Price List from Biotechnology Research Enterprises, S. A. Pty. Ltd., dated Nov., 1985, entitled "Photobiotin Acetate".

Converse, et al., Biochem., 8(11):4431–4436 (1969). Nov.

Chowdhry, Ann. Rev. Biochem., 48:293–325 (1979). no month available.

Erecinski, et al., Arch. Biochem. Biophys., 171:108–116 (1975). no month available.

Katzenellenbagen, et al., Biochem., 13(14):2986–2994 (1974). no month available.

Green, et al., "The Use of Fifunctional Biotinyl Compounds to Determine the Arrangement of Subunits in Avidin", Biochem. J. 125, 781–791 (1971). no month available.

Gorman, et al., "Transglutaminase Amine Substrates for Photochemical Labeling and Cleavable Cross–Linking of Proteins", J. Biol. Chem. 255, 1175–1180 (1980). Feb.

Darfler, et al., "Applications of Light–Sensitive Chemicals for Probing Biological Processes", Chap. 2 of *Chemistry and Biochemistry of Amino Acids, Peptides and Proteins*, vol. 5, pp. 31–93, Marcel Dekker, Inc., N.Y. (1978). no month available.

Friedberg, "Affinity Chromatography and Insoluble Enzymes", Chromatogr. Rev. 14, 121–131 (1971). Dec.

Bayley, et al., "Photoaffinity Labeling", Methods in Immunology XLIV, pp. 69–114, Acad. Press, N.Y., (1977). no month available.

CRC Handbook of Chemistry and Physics, 64th Ed., 1983–1984, p. 171. no month.

Heyman, et al., "Heparinized Polyurethanes: In Vitro and In Vivo Studies", J. Biom. Mat. Res., vol. 19, (1985), pp. 419–436. no month available.

Guire, "Stepwise Thermophotochemical Cross–Linking for Enzyme Stabilization and Immobilization", Enzyme Engineering, vol. 3, (1978), pp. 63–70. no month available.

SUBSTRATE SURFACE PREPARATION

This application is a continuation of application Ser. No. 07/816,771, filed Jan. 2, 1992, now abandoned, which is a continuation of Ser. No. 07/675,604 filed Mar. 25, 1991, now abandoned, which is a division of Ser. No. 07/447,802 filed Dec. 8, 1989, now U.S. Pat. No. 5,002,582, is a division of Ser. No. 07/223,149 filed Jul. 22, 1988, now abandoned, which is a CIP of Ser. No. 07/138,226 filed Dec. 24, 1987, now abandoned which is a CIP of Ser. No. 06/920,567 filed Oct. 17, 1986, now abandoned and is a CIP of Ser. No. 07/108,765 filed Oct. 15, 1987, now U.S. Pat. No. 4,973,495, which is a CIP of Ser. No. 06/428,074 filed Sep. 29, 1982, now U.S. Pat. No. 4,722,906.

BACKGROUND OF THE INVENTION

It is often desirable to provide the surface of an object with a polymeric coating to protect the surface or to provide the surface with properties of the polymer coating. For example, various paint-like coating compositions are employed to provide the surfaces of metals, wood and the like with thin, protective polymeric films.

The adhesion of polymeric films such as those described above to the surfaces to which they are applied are commonly largely mechanical. The surfaces often are roughened or otherwise prepared before a polymeric coating is applied so as to increase the degree of mechanical adhesion. Polymers are generally not chemically bonded to the surfaces upon which they are applied, and polymer coatings generally have not been used as coatings for devices which may be implanted in the human body or to devices which come into contact with body fluids during use, such as contact lenses. Coatings for objects such as these should adhere tenaciously to their surfaces even in the presence of body fluids and other liquids.

To improve the adhesion of certain polymer species to supporting surfaces, U.S. Pat. Nos. 4,663,232, 4,311,573, 4,595,632 and 4,589,964 teach that surfaces to be coated must be carefully prepared, as by precoating, using careful, often time-consuming procedures to receive polymer species.

SUMMARY OF THE INVENTION

We have discovered that polymer molecules and reactive chemical molecules such as monomers and oligomers may be provided with latent reactive groups covalently bonded to them such that when the molecules are brought into bonding proximity with a substrate such as a surface, the latent reactive groups can be energized to form, via free active specie generation, covalent bonds between these molecules and the substrate. The substrate to which the polymer molecules are to be so attached need not be specifically pretreated so as to add to it functional groups to which bonding occurs, and the invention provides a method by which such molecules may be readily attached to untreated substrates of various types.

Thus, in one embodiment, the invention relates to a method of providing a substrate, preferably a surface, with desired physical characteristics which comprises contacting the substrate with a composition comprising a plurality of molecules of a polymer possessing the desired physical characteristics, the polymer molecules each having covalently bonded thereto at least one latent reactive group. The latent reactive group is capable of generating an active specie such as a free radical in response to external stimulation to covalently bond the polymer molecule to the substrate, through the residue of the latent reactive group. The polymer molecule is so spatially oriented as to enable one or more of its latent reactive groups to come into covalent bonding proximity with the substrate surface, and the method includes the step of thereafter activating the latent reactive group by applying external stimulation to covalently bond the polymer molecule to the substrate. The external stimulation that is employed desirably is electromagnetic radiation, and preferably is radiation in the ultraviolet, visible or infra-red regions of the electromagnetic spectrum.

In another embodiment, the invention relates to a latent reactive polymeric composition which can be applied to a substrate such as a surface and covalently bonded to it by application of an external stimulus. The polymeric composition comprises a plurality of polymer molecules each having covalently bonded thereto at least one latent reactive group capable of active specie generation in response to applied external stimulation to covalently bond to the substrate, the polymer molecules being so spatially oriented as to enable their latent reactive groups to come into covalent bonding proximity with a surface or other substrate to which the coating composition is applied. Desirably, the coating composition includes a vehicle carrying the polymer molecules and within which the polymer molecules are permitted sufficient freedom of movement as to enable latent reactive groups of the polymer molecules to be positioned in bonding proximity with the substrate with which the coating composition is applied.

In yet another embodiment, the invention relates to a surface or other substrate bearing a plurality of polymer chains each covalently bonded to it through a residue of a latent reactive group, which latent group was initially capable of active specie generation in response to application of an external stimulus to covalently bond to the substrate; the polymer chains being present in sufficient quantity as to provide the surface or other substrate to which they are attached with one or more characteristics of the polymer.

In yet another embodiment, the invention relates to a method of providing a surface or other substrate with a plurality of polymer chains covalently bonded to it, the method comprising contacting the substrate with chemical, preferably polymerizable, reactive units such as monomers or oligomers each having covalently bonded to it a latent reactive group, and externally stimulating the latent reactive group to cause the same to covalently bond to the substrate via active specie generation. To the thus-bonded reactive units are covalently bonded one or more monomers, oligomers or polymers via grafting or via polymerization of monomers or oligomers to provide polymer chains, the resulting chains thus being covalently bonded to the substrate.

In a further embodiment, the invention relates to a method of forming a cross-linked polymer comprising providing each of a plurality of polymer molecules with at least one latent reactive group as above described, bringing the polymer molecules into reactive association with one another, and activating the latent reactive groups by application of an external stimulus to cause said groups to covalently bond to latent reactive group-free portions of others of the molecules. The reaction desirably occurs in a solvent solution of the polymer molecules, and the resulting cross-linked polymer molecules may thicken the solution, may form a gel, or may form a solid such as a film.

DESCRIPTION OF THE PREFERRED EMBODIMENT

The polymers of the invention may be natural or synthetic in origin. Such polymers include oligomers, homopolymers and copolymers resulting from addition or condensation polymerization, and natural polymers including oligosaccharides, polysaccharides, peptides, and proteins. The polymers may include several distinct polymer types, as prepared by terminal or side chain grafting. The polymers of the invention may include cellulose-based products such as hydroxyethyl cellulose, hydroxypropyl cellulose, carboxymethyl cellulose, cellulose acetate and cellulose butyrate, acrylics such as those polymerized from hydroxyethyl acrylate, hydroxyethyl methacrylate, glyceryl acrylate, glyceryl methacrylate, acrylic acid, methacrylic acid, acrylamide and methacrylamide, vinyls such as polyvinyl pyrrolidone and polyvinyl alcohol, nylons such as polycaprolactam, polylauryl lactam, polyhexamethylene adipamide and polyhexamethylene dodecanediamide; polyurethanes, polylactic acids, linear polysaccharides such as amylose, dextran, chitosan, and hyaluronic acid, and branched polysaccharides such as amylopectin, hyaluronic acid and hemi-celluloses. The polymeric species are chosen so as to exhibit one or more properties desired for the surface or other substrate to which the polymer molecules are bonded. For example, it may be desired in some instances to provide surfaces with very hydrophilic properties, in which case polymer species such as hyaluronic acid may be employed. The polymer polyethylene glycol may be employed to repel proteins as from a contact lens surface. Heparin, a polysaccharide, may be used to impart antithrombogenic characteristics, and chitosan may be employed to provide hemostatic properties.

The physical characteristics of the polymer molecules employed in the present invention are generally derived from the nature of the molecular chains themselves. Thus, polyvinyl alcohol, for example, which bears a plurality of hydroxyl groups and which is generally water soluble, provides hydrophilic characteristics to a surface or other substrate to which it is covalently bonded through the method of the invention. The polymer molecules of the invention desirably are substantially free of biologically active groups that are either added to the polymer molecules after polymerization or that are not normally contained in the precursor monomers or in identical, repeating units of the polymer. The polymer molecules that are employed in the invention desirably have extended chain lengths of at least about 10 Angstroms, preferably at least 25 Angstroms, and most preferably at least about 50 Angstroms.

Most preferably, the polymer molecules include end portions which are free from latent reactive groups and which end portions themselves have extended lengths (measured from the nearest latent reactive group) of at least 10 Angstroms and preferably at least 25 Angstroms, and most preferably at least 50 Angstroms. In this manner, the free polymer molecule end portions may extend as desired away from the surface or other substrate to which the molecule is attached to provide appropriate physical or other characteristics. The polymer molecules themselves preferably have molecular weights of at least about 400, and desirably are generally hydrophilic in nature, the polymers preferably being soluble in water to the extent of at least approximately 0.5% by weight at 25° C. "Extended length", as used herein, refers to the length that a polymer chain would have if it were stretched out to its maximum length, observing proper bond angles between adjacent atoms. Polyethylene glycol, hyaluronic acid, collagen, chitosan, heparin, and polyvinyl alcohol are particularly preferred polymers.

The polymer molecules employed in the invention carry one or more latent reactive groups covalently bonded to them. The latent reactive groups, broadly defined, are groups which respond to specific applied external stimuli to undergo active specie generation with resultant covalent bonding to an adjacent support surface. Latent reactive groups are those groups of atoms in a molecule which retain their covalent bonds unchanged under conditions of storage but which, upon activation, form covalent bonds with other molecules. The latent reactive groups generate active species such as free radicals, nitrenes, carbenes, and excited states of ketones upon absorption of external electromagnetic or kinetic (thermal) energy. Latent reactive groups may be chosen to be responsive to various portions of the electromagnetic spectrum, and latent reactive groups that are responsive to ultraviolet, visible or infrared portions of the spectrum are preferred. Latent reactive groups as described are generally well known.

The azides constitute a preferred class of latent reactive groups and include arylazides

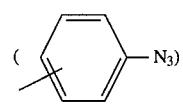

such as phenyl azide and particularly 4-fluoro-3-nitrophenyl azide, acyl azides

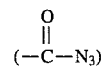

such as benzoyl azide and p-methylbenzoyl azide, azido formates

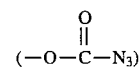

such as ethyl azidoformate, phenyl azidoformate, sulfonyl azides

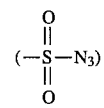

such as benzenesulfonyl azide, and phosphoryl azides,

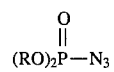

such as diphenyl phosphoryl azide and diethyl phosphoryl azide. Diazo compounds constitute another class of latent reactive groups and include diazoalkanes (—CHN$_2$) such as diazomethane and diphenyldiazomethane, diazoketones

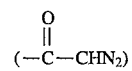

such as diazoacetophenone and 1-trifluoromethyl-1-diazo-2-pentanone, diazoacetates

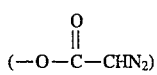

such as t-butyl diazoacetate and phenyl diazoacetate, and beta-keto-alpha-diazoacetates

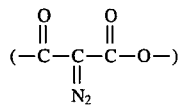

such as t-butyl alpha diazoacetoacetate. Other latent reactive groups include the aliphatic azo compounds such as azobisisobutyronitrile, the diazirines

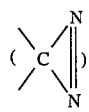

such as 3-trifluoromethyl-3-phenyldiazirine, the ketenes (—CH═C═O) such as ketene and diphenylketene and photoactivatable ketones such as benzophenone and acetophenone. Peroxy compounds are contemplated as another class of latent reactive groups and include dialkyl peroxides such as di-t-butyl peroxide and dicyclohexyl peroxide and diacyl peroxides such as dibenzoyl peroxide and diacetyl peroxide and peroxyesters such as ethyl peroxybenzoate.

Upon activation of the latent reactive groups to cause covalent bond formation to the surfaces to which polymer molecules are to be attached, the polymer molecules are covalently attached to the surfaces by means of residues of the latent reactive groups. Exemplary latent reactive groups, and their residues upon activation, are as follows:

| Latent Reactive Group | Residue Functionality | |
|---|---|---|
| aryl azides | amine | R—NH—R' |
| acyl azides | amide | R—C(═O)—NH—R' |
| azidoformates | carbamate | R—O—C(═O)—NH—R' |
| sulfonyl azides | sulfonamide | R—S(═O)(═O)—NH—R' |
| phosphoryl azides | phosphoramide | $(RO)_2P(=O)$—NH—R' |
| diazoalkanes | new C—C bond | |
| diazoketones | new C—C bond & ketone | |
| diazoacetates | new C—C bond & ester | |
| beta-keto-alpha-diazoacetates | new C—C bond & B-ketoester | |
| aliphatic azo | new C—C bond | |
| diazirines | new C—C bond | |
| ketenes | new C—C bond | |
| photoactivated ketones | new C—C bond & alcohol | |
| dialkyl peroxides | ethers | |
| diacyl peroxides | esters & new C—C bonds | |
| peroxyesters | ethers, esters, and new C—C bonds | |

The polymers and oligomers used in the invention may have one or more latent reactive groups. Desirably, the polymers have at least one latent reactive group per molecule with the ratio of reactive groups extended polymer length, in Angstroms, ranging from about 1/10 to about 1/700 and preferably from about 1/50 to 1/400.

As will be noted from the foregoing description, photoreactive latent reactive groups are for the most part aromatic and hence generally are hydrophobic rather than hydrophilic in nature.

The latent reactive groups and the polymer molecules to which they are bonded may have substantially different solvophilic properties. For example, the latent reactive groups may be relatively hydrophobic, whereas the polymer molecules may be relatively hydrophilic; when solution of the molecules is contacted with a relatively hydrophobic surface, it is believed that the latent reactive groups, being hydrophobic, tend to orient nearer the surface so as to improve bonding efficiency when the latent reactive groups are activated. The preferred latent reactive groups are benzophenones, acetophenones, and aryl azides.

The loading density of polymers upon a surface may be improved by a process in which a latent reactive molecule (a molecule having a latent reactive group) is first brought into close association (as by means of a solvent solution) to a surface, and thereafter the polymer to be bonded to the surface is brought into contact with and is covalently bonded to the latent reactive molecule, as to a reactive group different from the latent reactive group. Thereafter, the latent reactive groups may be activated to cause them to covalently bond to the surface to thereby link the polymers to the surface. This procedure appears to work particularly well when the latent reactive group is solvophilically compatible with (e.g., similar to) the surface and wherein the polymer is relatively solvophilically incompatible with the surface but is more compatible with a portion of the latent reactive group. Reference is made to Example IX below as being illustrative of this procedure.

If desired, polymer chains may be provided upon a surface or other substrate by first covalently bonding to the substrate through a latent reactive group a monomer, oligomer or other reactive chemical unit. To the thus-bonded reactive units are covalently bonded monomers or oligomers in a polymerization reaction or polymers via covalent bonding (grafting) of the reactive units onto the polymer chains.

The reactive chemical units of the invention carry covalently bonded thereto latent reactive groups as described herein for covalent attachment to a non-pretreated surface or other substrate. These molecules are characterized as having reactive groups capable of covalent bonding to polymer molecules of a polymer having the desired characteristics, or of entering into a polymerization reaction with added monomers or oligomers to produce polymer chains having the desired characteristics. Reactive chemical molecules capable of covalently bonding to polymer molecules include not only monomers and oligomers of various types but also molecules having such functional groups as carboxyl, hydroxyl, amino, and N-oxysuccinimide, such groups being reactive with reactive groups carried by the polymer chain to bond to the chain. The reactive chemical molecules are preferably monomers or oligomers and most preferably are ethylenically unsaturated monomers capable of entering into an addition polymerization reaction with other ethylenically unsaturated monomers. Particularly preferred are the acrylate and methacrylate monomers which are the esterification products of acrylic or methacrylic acid and hydroxy-functional latent reactive groups. Examples of such molecules include 4-benzoylbenzoyl-lysyl-acrylate.

Utilizing reactive chemical units bearing latent reactive groups, one will desirably first coat a surface or other substrate with a solvent solution of such molecules. Upon removal of solvent, the application of an appropriate external stimulus such as U.V. light will cause the molecules to covalently bond, through the latent reactive groups, to the substrate. The substrate may then be appropriately contacted with a solution containing the desired polymer, monomer or oligomer molecules to cause bonding to these molecules. For example, if the reactive chemical unit molecule is carboxyl functional, it may be reactive with, and covalently bonded to, an appropriate hydroxyl-functional polymer such as dihydroxy polyethylene glycol. If the reactive chemical molecule is a monomer or oligomer, e.g., a methacrylate monomer, the substrate to which the molecule is covalently bonded may be contacted with a solution of addition-polymerizable monomers such as hydroxyethyl methacrylate and a free-radical addition polymerization initiator such as dibenzoyl peroxide under addition polymerization conditions to result in the growth of polymer chains from the monomer molecules bound covalently to the substrate. Once the desired polymerization has occurred, the substrate may be washed to remove residual monomer, solvent and non-bound polymer that was formed.

The term "substrate" refers to any chemical moiety to which polymer molecules are to be attached through activation of latent reactive groups. The substrate may take the form of molecules in a solution, but more desirably, the substrate comprises a definable surface such as the tangible surface of a contact lens or surgical implant, or the surface provided by small particles in an emulsion or other suspension or as a powder, or the surface defined as the interface between two substantially distinct phases, such as two immiscible liquid phases or the surface of a soft gel. Although the polymer molecules may be attached to the same or different polymer molecules in a solution, as described more fully below, the invention provides the particular advantage of providing means by which non-pretreated definable (e.g., solid) surfaces may simply and rapidly be provided with covalently bonded-on polymer coatings in a simple, rapid and hence economical manner.

"Hydrophilic" and "hydrophobic" are used herein to describe compositions broadly as water-loving and water-hating, respectively, in line with the following observations: Hydrophilic compounds are usually relatively polar and often are ionizable. Such compounds usually bind water molecules strongly. Hydrophobic compounds are usually relatively non-polar and non-ionizing. Hydrophobic surfaces will generally cause water molecules to structure in an ice-like conformation at or near the surface. "Hydrophobic" and "hydrophilic" are relative terms, of course, and are used herein in the sense that various compositions, liquids and surfaces may be hydrophobic or hydrophilic relative to one another. A discourse on the subject is found in Hoffman, *Letter to the Editor: A General Classification Scheme for "Hydrophilic" and "Hydrophobic" Biomaterial Surfaces*, J.Biol. Mat. Res. 20, pp ix–xi (1986), the teachings of which are incorporated herein by reference.

The loading density resulting from attachment of polymer molecules to a surface or other substrate in accordance with the invention may be regulated in several ways. First, the degree of activation of latent reactive groups is generally a function of the quantity of the external stimulus that is applied, and thus the extent of covalent bonding through the latent reactive groups may be regulated by regulating the intensity and time of application of the applied stimulus. Regulation of the applied stimulus is particularly easy when the stimulus is actinic radiation; one can readily regulate the amount of radiation to which the latent reactive groups are exposed. Loading density may also be regulated by adjusting the capacity of polymer molecules of the invention to bring their latent reactive groups into bonding proximity with a surface. Thus, one may regulate the viscosity of a solution of polymer molecules in an appropriate solvent as well as the solubility of polymer in the solvent. Yet another factor is the concentration of polymer molecules in a coating composition.

As will be understood from the above discussion and from the examples which follow, the invention permits a substrate, particularly a solid surface, to be provided with covalently attached polymer molecules in sufficient loading density or quantity as to provide an "effective" surface having the physical properties of the added polymer rather than those differing physical properties of the uncoated solid surface. In this manner, for example, the hydrophobic surface of polystyrene may be rendered comparatively hydrophilic through the covalent bonding of e.g., the hydrophilic polymer polyethylene glycol to the polystyrene surface.

In a preferred embodiment, the method of the invention is practiced on a surface or other substrate that has not been pretreated. As used herein, the terms "pretreatment" and "pretreated" refer to the addition to a surface or other substrate of functional groups which are chemically involved in the covalent bonds subsequently formed upon activation of latent reactive groups. Substrates such as solid surfaces may be pre-washed; of course, to remove surface contamination and may be modified as desired to affect solvophilic characteristics without adding functional groups that are involved in covalent bond formation with latent reactive groups. For example, polystyrene surfaces may be washed and then exposed to hydroxyl ions in known water vapor plasma contact procedures so as to add hydroxyl groups to the surface solely for the purpose of rendering the surface more readily wetted by aqueous solutions, the hydroxyl groups not being involved in subsequent covalent bond formation with the surface upon latent reactive group activation. Avoidance of pretreatment steps, as above defined, leads not only to important processing economies but also avoids technical problems associated with the attachment of bond-forming reactive groups to surfaces at uniform loading densities.

The invention may be more easily appreciated by reference to the following non-limiting examples, in which parts are expressed by weight unless otherwise indicated.

EXAMPLE I

Modification of the Surfaces of Contact Lenses and Introcular Lens Implants

The experiments described in this example involved preparations of hydrophilic polymers that are covalently bonded to contact lens surfaces through latent reactive groups carried by the polymers.

Preparation of Photolabeled Polyethylene Glycols Polyethylene glycols of molecular weights 1000 (PEG-1000) and 4000 (PEG-4000) were labeled with fluoro-2-nitro-4-azidobenzene (FNAB) by modification of the phase transfer method of Kimura, and S. Regen, Journal of Organic Chemistry 48; 195 (1983) the teachings of which are incorporated by reference herein. Briefly, the phase-transfer synthesis of 4-azido-2-nitrophenyl polyethylene glycol (ANP-PEG) involved the mixture of 60% aqueous potassium hydroxide ("KOH")/toluene with FNAB and PEG, followed by extraction and thin-layer chromatographic (TLC) purification as described below.

ANP-PEG-1000

ANP-PEG-1000 was prepared by adding 0.3 mmole PEG-1000 to 5 mls 60% KOH and 0.15 mmole FNAB to 10 ml toluene. This reaction mixture was rapidly stirred at room temperature for 16 hours. The product was isolated from the organic layer. TLC in 85/15/1/1 chloroform/methanol/$H_2O$/acetic acid or ammonium hydroxide separated mono-and di-substituted derivatives of ANP-PEG-1000 from unlabeled PEG. The band corresponding to ANP-PEG-1000 (lower $R_f$ value) was extracted from silica gel with TLC solvent and azeotrophed to remove residual acid or base. The final product was soluble in water.

ANP-PEG-4000

ANP-PEG-4000 was prepared by the same procedure as that described above except that the reaction mixture was rapidly stirred at 50° C. to ensure all reagents remained in solution during the course of the reaction.

Preparation of Photolabeled Jeffamines

Polyoxypropylenepolyamines and polyoxyethylenepolyamines (referred to as "Jeffamines", a trademark of Jefferson Chemical Co., Inc.) were photolabeled by coupling the N-oxysuccinimide ("NOS") esters of ANP-EACA (epsilon-aminocaproic acid), BBA (4-benzyl benzoic acid) and nBBA (4-(3nitrobenzyl)benzoic acid) to the polymers. These NOS-derivatives were added to a two molar excess of Jeffamine in very dry (high purity) solvents (ANP-EAC-NOS in dry tetrahydrofuran, BBA-NOS in dry dioxane or dimethylformamide and nitro BBA-NOS in dry dioxane or dimethylformamide). After 16 hours of reaction at room temperature in the dark, the products were isolated by TLC in 85/15/1/1/chloroform/methanol/$H_2O$/acetic acid. Mono-substituted Jeffamine derivatives were extracted with the TLC solvent and azeotroped with water to remove the residual acetic acid. The ANP-EAC-Jeffamine, BBA-Jeffamine, and nBBA-Jeffamine products were water soluble.

Preparation of ANP-Hyaluronic Acid

The terminal sugar of human placental hyaluronic acid ($MW_{app}$100–130,000) was activated by the periodate procedure described in E. Junowicz and S. E. Charm, "The Derivatization of Oxidized Polysaccharides for Protein Immobilization and Affinity Chromatography," *Biochimica et Biophysica Acta*, Vol. 428:157–165 (1976), incorporated herein by reference. This procedure entailed adding sodium or potassium periodate to a solution of hyaluranic acid thus activating the terminal sugar. The hyaluronic acid was added to a 10-fold excess of Jeffamine and allowed to react 4 hours at room temperature. The linkages were stabilized by reduction with sodium cyanoborohydride, followed by exhaustive dialysis to remove non-bound Jeffamine. A 10-fold molar excess of ANP-EAC-NOS in DMF was added to the Jeffamine-hyaluronate in 0.1M carbonate, pH 9.0, by syringe drive. This addition required 16 hours and was conducted at room temperature in the dark. The excess ANP-EAC-NOS and ANP-EAC-Jeffamine was removed by gel filtration chromatography. The integrity of the azide group, which is required for photocoupling of the moiety to the contact lens polymer backbone, was analyzed by infrared spectroscopy to detect the azido function of the ANP group, a polyethylene glycol assay to detect the Jeffamine spacer, and a modified carbazole assay described in T. Bitter and H. Muir, *Analytical Biochemistry* Vol. 4: 330–334 (1962) and incorporated herein by reference to determine the uronic acid content of the derivative.

The polyethylene glycol assay was developed using the Dragendorff reagent (tetraiodobismuthic acid-barium chloride). A 5-ml portion of stock reagent (425-mg bismuth nitrate, 10-gm potassium iodide in acetic acid and water) was added to 10-ml 10% barium chloride in water and a background reading at 516/nm was noted. Then 0.1-ml of the sample was added and the contents mixed by inversion of the cuvette. A reading was taken at 516/nm after 1 minute of incubation. The values were compared to a standard curve.

The carbazole assay was performed as follows. A 3.0 ml portion of sulfuric acid reagent (0.025M sodium tetraborate in sulfuric acid) was cooled to −70° C. A 0.5 ml portion of sample was layered onto the acid and the mixture was stirred (30 min.) until it reached room temperature. The tubes were heated at 100° C. (10 min.), a 0.1 ml aliquot of carbazole reagent (0.125% carbazole in absolute ethanol) was added, the tube contents were mixed (5 min.), heated at 100° C. (15 min.), then cooled to room temperature in an ice bath. The samples were analyzed spectrophotometrically at 530 nm against a sulfuric acid reagent blank. The results were compared to a standard curve constructed with 4–40 ug/ml glucuronolactone standards. The assay was sensitive to detecting 20 pmole of hyaluronic acid.

The fractions containing one ANP, one Jeffamine and one hyaluronate molecule were pooled and used.

Preparation of Photolabeled Hyaluronic Acid, Methyl Cellulose and Chondroitin Sulfate Sodium hyaluronate was dissolved in deionized $H_2O$ to give a 1% polysaccharide w/v solution. This 1% solution was then dialyzed against 0.05M MES (2-(N-Morpholino) ethanesulfonic acid), pH 4.0 to convert the sodium salt to the acid form of hyaluronic acid. A 0.135 mmole portion of ANP-EAC-Jeffamine or BBA-EAC-Jeffamine solid was added to the 10-ml of 0.5% hyaluronic acid and a thorough mixture of the two reagents was made by rotary stirring for 30 minutes. To this mixture was added 190 mg of EDC (1-ethyl-3-(3-dimethylaminopropyl)carbodiimide) and 40 mg Sulfo-NHS (N-hydroxysulfosuccinimide) at thirty minute intervals for a total of four additions. Thirty minutes after the final addition, the volume was reduced by one-half by rotary evaporation and the reaction was left to continue an additional 12 hours at 4° C. After the 12 hours of incubation, the reaction mixture was transferred to a dialysis bag of 12,000 MW cut-off. The mixture was then dialyzed against four changes of deionized $H_2O$ to remove non-covalently bound ANP-EAC-Jeffamine, followed by dialysis against saline containing 0.001% thimerasol preservative. This reaction product was then analyzed by the carbazole reaction to assess remaining uronic acid residues, and UV spectroscopy to quantitate the photogroup loading on the polysaccharide. A loading density of one out of every 20 carboxyl groups modified with photogroup was obtained by this process. Photolabeled carboxymethyl cellulose and condroitin sulfate can be prepared by similar procedures.

Preparation of Photolabeled Collagen

Human placenta Type IV collagen (available from Sigma Pharmacueticals) was dissolved at a 1 mg/ml concentration in 0.1M borate, pH 9.0. ANP-EAC-NOS in DMF, BBA-sulfo-NOS in dioxane or nitro BBA-NOS in dioxane was slowly added to the collagen solution in a 50× molar excess by syringe drive at 4° C. in the dark over 16 hours. After the addition was complete, the mixture was stirred 4 hours in the cold. The collagen product was dialyzed against 4 changes of PBS then centrifuged to remove insoluble material. The supernatant was measured spectrophotometrically at 260 nm, 280 nm and 462 nm to assess the photogroup/protein ratio.

Preparation of Photolabeled Proteinases

ANP-EAC-NOS, BBA-NOS and nBBA-NOS photogroup dissolved in organic solvent at 25 mg/ml concentrations, were added in 50 molar excess to papain (papaya, MW 23,426) by syringe drive at 4° C. in the dark over 16 hours. After addition of the photogroup was completed, the mixture was stirred an additional 4 hours, then dialyzed in PBS to remove uncoupled photogroups. After dialysis, the product was centrifuged to remove insoluble material. The supernatant was measured spectrophotometrically at 260 nm, 280 nm, and 462 nm to estimate the photogroup/protein ratio.

Photocoupling of Polymers to Lens Surfaces

The photolabeled polymer agents obtained above were added to the contact lens materials described in Table 4 at a concentration of 250–1000 pmole polymer/contact lens. The solution was allowed to adsorb onto the contact lenses at room temperature in the dark for 3 hours. The polymers were then covalently linked to the plastic by photolysis for 12 hours at the appropriate wavelength (450 nm for ANP and 320 nm for BBA and nBBA derivatives). After photolysis, the contact lenses were washed with 5×5 ml of normal saline (0.85% NaCl) to remove non-covalently linked groups.

Radiolabeled groups may be coupled to the lens materials, and the lens pieces treated with tetrahydrofuran followed by DMSO to release the radiolabel from the solid surface. Scintillation fluor is then added and the amount of polymer/$cm^2$ is determined by liquid scintillation spectroscopy. Representative results are shown in Table 1.

TABLE 1

| Photolabeled Polymer | Contact Lens Material | ng/$cm^2$ |
| --- | --- | --- |
| ANP-PEG-1000 | Polyvinyl chloride | 19.96 |
| | Sofspin (polymacon) | 33.45 |
| | Permaflex | 33.97 |
| | Vistamarc | 34.26 |
| | Lidofilcon | 63.12 |
| | Silicone | 33.97 |
| | **Polymacon Button | 2408.60 |
| ANP-PEG-4000 | Sofspin (polymacon) | 108.24 |
| | Permaflex | 171.44 |
| | Silicone | 682.40 |
| | **Polymacon Buttons | 6296.00 |
| nitro BBA-PEG-2000 | Polyvinyl Chloride | 46.40 |
| | Sofspin | 26.28 |
| | Permaflex | 16.42 |
| | Silicone | 191.22 |
| | **Polymacon Buttons | 7476.00 |
| BBA-PEG-2000 | Silicone | 226.40 |
| | **Polymacon Buttons | 8070.20 |
| ANP-Hyaluronic acid | Silicone | 25.00 |
| | **Polymacon Buttons | 130.95 |

*Values were averaged from replicates of 10
**Polymacon loads are based on total volume, $cm^3$, rather than surface area.
Sofspin contacts are made of polymacon with about 38.6% water and are a trademarked product of Bausch & Lomb, Inc.
Permaflex contacts are made of poly(hydroxyethylmethacrylate) with about 74% water and are a trademarked product of Coopervision, Inc.
Vistamarc contacts are made of poly(hydroxyethylmethacrylate) with about 58% water and are a trademarked product of Johnson & Johnson.
Lidofilcon contacts are made of poly(hydroxyethylmethacrylate) with about 70% water and are a product of Bausch & Lomb, Inc.

The values in Table 1 are expressed as ng of polymer per square centimeter of surface. The ANP derivatives coupled at higher load densities than the nBBA-Jeff on the hydrogel contact lens materials. These results were reversed for the silicone compound.

In Vitro Protein Adsorption Studies

Artificial human tears were prepared according to the formula found in B. P. Gloor, "The Lacrimal Apparatus" in *Adler's Physiology of the Eye: Clinical Applications* (R. A. Moses, ed.), C. V. Mosby Co., St. Louis, Mo. (1981) the teachings of which are incorporated herein. As indicated in that reference the major proteins present in human tears are serum albumin (HSA), gamma-globulin (HGG), and lysozyme (LYZ). The major sterols present in human tears are cholesterol and cholesterol esters.

$^3$H Proteins

The protein components were tritiated by reductive methylation with formaldehyde and tritiated sodium borohydride as described in N. Jentoft and D. C. Dearborn, *Journal of Biochemistry*, Vol. 254: 4359–4365 (1979) and incorporated herein by reference. Briefly, the proteins in 1 mg/ml concentration in 0.1M HEPES, pH 7.4 were methylated by reacting with formaldehyde and tritiated sodium borohydride, rocking at 22° C. for about 2 hours. The product was dialyzed against PBS in 0.01M phosphate, 0.15M sodium chloride, pH 7.4, and affinity purified on gelatin sepharose. Bound agent was eluted with 1M sodium bromide 0.02M sodium acetate, pH 5.0, then dialyzed against PBS, pH 7.4.

Preparation of Artificial Tears

The radiolabeled proteins described above were used in preparation of artificial tears. One of the radiolabeled proteins or the tritiated cholesterol was included in each tear mixture. The other components were not radiolabeled. The contact lens materials were incubated in the artificial tear solution for one week at 37° C. with gentle agitation. At the end of this time the lens materials were washed with 5×10 ml of 0.85% NaCl. The amount of protein adsorbed to the lens materials was then determined by liquid scintillation counting.

Reduction in total protein deposition reached 85% in ANP-PEG-1000 modified Sofspin lenses. The overall protein amounts were reduced for all lens materials except ANP-1000-OH coated Polymacon buttons, ANP-4000-OH coated polymacon buttons and ANP-hyaluronate coated polymacon buttons. These poor results were all obtained with virgin polymacon materials which appears to react differently than polymacon contact lenses, such as Sofspin lenses. Overall, these in vitro protein deposition studies demonstrated significant to dramatic decreases in protein deposition from artificial tears on various contact lens materials during a one week period.

Amino Acid Analysis

Control and surface modified lenses were incubated in the artificial tear solution for one week at 37° C. with gentle agitation. The lenses were washed with 5 10 ml washes of 0.85% NaCl, then hydrolyzed with 6N HCl and the hydrolysates subjected to standard amino acid analyses on an amino acid analyzer. Total amino acid content of control and surface modified lenses were compared to each other. Reduction in total amino acid content indicated a reduction in protein absorption.

The total amino acid analyses of the acid hydrolyzed contact lenses are given in Table 2. These results are expressed as total amino acids in nmole/ml. These results again indicated that the ANP-PEG-1000, ANP-PEG-4000 and nBBA-Jeff modifications of Sofspin polymacon lenses reduced the deposition of proteins on the lenses after 7 days of incubation in artificial human tears.

TABLE 2

Total Amino Acid Analyses from Artificial
Tear Deposits on Contact Lenses

| Contact Material | Biocompatible Agent | Total Amino Acids nmol/lens | % Reduction |
|---|---|---|---|
| Sofspin | ANP-PEG-1000 | 62.8 | 59.7 |
|  | ANP-PEG-4000 | 136 | 12.4 |
|  | nBBA-Jeff | 105 | 32.3 |
|  | Control | 156 | — |
| Permalens | ANP-PEG-1000 | 169 | 32.5 |
|  | ANP-PEG-4000 | 210 | 15.9 |
|  | nBBA-Jeff | 181 | 27.5 |
|  | Control | 250 | — |

EXAMPLE II

Preparation of Monofunctional (Photoreactive) Polyethylene Glycol

Dihydroxy PEG 1450, 0.125 moles, was dissolved in 800 ml of toluene, followed by removal by distillation of 200 ml of solvent to provide azeotropic removal of water. Triethylamine, 0.143 moles, was then added, followed by the addition of 0.0625 moles of the acid chloride of 4-benzoylbenzoic acid (Aldrich B1,240-7). The mixture was stirred for 2 hours at room temperature. The crude reaction mixture was filtered through a Celite pad to remove the hydrochloride salt of triethylamine and the toluene was removed under reduced pressure.

The crude product was then dissolved in water (2 ml water/1 g product) and solid sodium chloride was added (50 mg NaCl/1 ml water). After adjusting the pH to 7 using solid sodium bicarbonate, toluene (1 ml/1 g product) and isopropyl alcohol (1 ml/5 g produce) were added and the layers were thoroughly mixed. This extraction was repeated until no more disubstituted PEG appeared in the organic phase by TLC as outlined in Example I. The aqueous layer was then briefly evaporated under reduced pressure (5% volume reduction) to remove organic solvents. The aqueous solution was then saturated with sodium chloride and extracted with toluene (1 ml/1 g solution) until all monosubstituted PEG was removed. Typically seven to eight extractions are required for complete removal of the monosubstituted PEG. The combined organic extracts were washed with saturated sodium chloride to remove any residual dihydroxy PEG and then were dried over anhydrous sodium sulfate.

The solvent was removed under reduced pressure and the product was redissolved in a small volume of toluene (1 ml toluene/5 g product). The product was precipitated by the addition of diethyl ether (5 times volume of toluene) and cooling on an ice bath. Final filtration and drying of sample gave a 48% yield of a white solid.

EXAMPLE III

Polyethylene Glycol-Coated Ocular Prostheses.

Ocular prostheses (artificial eyes) are generally made from poly methylmethacrylate. Ocular prostheses were inspected, cleaned and polished by an ocularist, and were then sprayed with a methanol solution containing 0.3% of the BBA-PEG-1450 derivative as described in Example II. The spray volume was just sufficient to completely wet the surface of the prostheses.

The BBA latent reactive groups were activated by UV radiation to form an excited state which abstracts a hydrogen from the acrylic substrate to covalently couple the PEG to the acrylic surface. This UV activation was carried out under an Electrolite Model ELC 4000 which illuminates the prostheses at 1.5 microwatts/square centimeter for a period of three minutes. The prostheses were cleaned to remove excess reagent and then returned to the patient.

When the prostheses were placed in the eyes of patients, the patients reported the initial sensation was "different", "more comfortable", "cool", and "feels like [their] natural eye". Patients have been able to distinguish the effect of the coating after three months of continuous wear.

EXAMPLE IV

Preparation of Succinimidyl 6-(4-Benzoylbenzamido Hexanoate

The acid chloride of 4-benzoylbenzoic acid, 0.041 moles, was dissolved in 150 ml of toluene and to that mixture was added a solution of 0.041 moles of 6-aminocaproic acid in 125 ml of 1N sodium hydroxide. The mixture was stirred vigorously for 45 minutes at room temperature during which time a precipitate formed. The product was then acidified with 125 ml of 1N HCL and extracted with 3×150 ml of ethyl acetate. The combined organic extracts were dried over anhydrous magnesium sulfate. After removal of solvent, the final product was recrystallized from toluene - ethyl acetate to give an 84% yield of a white solid, melting range 106°–109° C. A portion of the above amide product, 0.0147 moles, was dissolved in 100 ml of dry dioxane, followed by the addition of 0.0270 moles of N-hydroxysuccinimide. The reaction mixture was protected from moisture by a drying tube and was cooled to 0° C. A solution of 0.0270 moles of dicyclohexylcarbodiimide in 3 ml of dry dioxane was added over a 5 minute period. The mixture was then stirred overnight with slow warming to room temperature.

The dicyclohexylurea byproduct was removed by filtration and the dioxane was removed under reduced pressure. The product was diluted with 50 ml of ethanol and was evaporated again to dryness under reduced pressure to aid in the removal of the dioxane. The white solid was then recrystallized twice from ethanol to give a nearly quantitative yield of the activated ester, melting range 120°–122° C.

EXAMPLE V

The compound of Example IV is reacted with tritiated Human Type IV collagen by the following method: Tritiated Type IV collagen (previously dialyzed against borate-buffered saline at a concentration of 4 milligrams per milliliter) is mixed 10/1 by volume with 1 Molar sodium carbonate (pH 9). The compound of Example IV is dissolved in dry dimethyl formamide at 6 milligrams per milliliter and 8.0 mls of the resulting solution is added (over three hours) via syringe drive to 28 mls of a gently stirred (4° C.) solution of the Type IV collagen described above. The mixture is allowed to continue stirring for an additional hour. All material, including the precipitate that forms is dialyzed against several changes of phosphate buffered saline. The resultant reagent (which is insoluble) is suspended in deionized water and the pH is adjusted to 4 with dilute hydrochloric acid at which point the material goes into solution. The resultant reagent is applied to polystyrene tissue culture surfaces at a concentration of 13 ug of collagen/square cm and photoactivated in the same manner as the prosthesis in Example II. As a control, identical polystyrene tissue culture surfaces are treated with the same concentration of tritiated Human Type IV collagen without the photo groups attached. Both sets of surfaces are identically washed for 0.5 hour with five changes of a 0.1% solution of Tween 20 to remove unbound collagen.

The resultant washed surfaces are counted to show a several fold increase in retention by the photoderivatized collagen as compared to the control underivatized collagen.

Polystyrene tissue culture surfaces similarly prepared but using non-tritiated collagen are evaluated in actual tissue culture using fetal bovine corneal endothelial cells. The tissue outgrowth is several fold greater than the control, indicating creation of a more tissue compatible surface.

EXAMPLE VI

The ability to repel proteins by surfaces is a desired goal for many blood comparability applications (eg. in vivo blood sensors), and immuno gamma globulin (IgG) is a common blood protein which binds very tenaciously to plastics, especially polystyrene.

The BBA-PEG-1450 described in Example I, in a methanol solution, is sprayed into 96 well polystyrene microtiter plates at a concentration of 3000 ng of reagent per well. The methanol is allowed to evaporate off before the plates are photoactivated as described in Example II.

The wells are evaluated by absorbing Human IgG and evaluating the levels of absorption by standard ELISA methodology using an alkaline phosphatase enzyme coupled to anti-IgG. The PEG coated wells absorb only 20% of the IgG level of that absorbed onto untreated wells, indicating the ability to repel a very tenaciously absorbable blood protein.

EXAMPLE VII

4-Benzoylbenzoyl-lysyl-acrylate (BBA-LYS-AC) is prepared by reacting N-epsilon-t-BOC-L-lysine with 4-benzoylbenzoyl chloride, then deblocking the epsilon-amino group with 3N HCl in ethyl acetate for one hour at room temperature followed by reaction with acryloyl chloride at pH 9.0. This reagent is coated onto silicone contact lenses by incubating the reagent solution in 50% ethanol in 0.1M bicarbonate buffer at pH 9.5 for two hours at room temperature, then exposing to high intensity light at 305 nm. The acrylate is the polymerization site. A solution of 5% hydroxyethylmethacrylate in 0.1M bicarbonate buffer at pH 9.0 is then polymerized on the lenses using 2,2'-azobisisobutyronitrile as catalyst. The polymerization reaction is allowed to proceed for one hour at room temperature, after which the uncoupled polymer is removed by washing the plates. This procedure improves wettability of the lenses.

EXAMPLE VIII

Hyaluronic acid was derivatized with the ANP-EAC-PEG-amine of Example I to result in a substitution level of one photo-group per 5 carboxyl groups on the polysaccharide. A 0.5% solution of this HA derivative was used to prepare a film of this material on glass or silicone materials. After application and drying, the film was cross-linked by exposure to high intensity light at 320 nm for three minutes. After photolysis, the film was lifted from the form by hydration with deionized water. The film maintained its integrity in water, was translucent, and retained mechanical stability allowing it to be picked up with a forceps and handled. The photochemical cross-linking of this material resulted in the construction of a film with greatly reduced rate of dissolution in aqueous systems.

This film has utility in wound healing and drug delivery in ophthalmic applications.

EXAMPLE IX

It is known that small polypeptide subunits of cell attachment factors such as those used in Example V are actually responsible for the cell response by activating specific cellular receptor sites. Immobilization of these subunits onto a surface should elicit responses similar to the actual cell attachment factors if they are so immobilized without significantly altering their chemical stereochemistry so that they retain the properties recognized by the cells.

The polystyrene tissue culture "slips" as used in example 5 were soaked for two hours in a solution containing 1.5 micrograms of the compound of Example 4 dissolved into 133 microliters of methanol. The slips are removed and the methanol solvent is allowed to evaporate in air. A solution of 200 micrograms of fibronectin peptide (FP) subunits per milliliter of 0.1M bicarbonate (pH 9.0) in water was prepared. To one side of the polystyrene slip (0.5×1.0 cm) was added enough of the fibronectin peptide solution (75 microliters) to completely cover the entire surface. The slip maintained for 4 hours at 4° C. Without removing the solution the slip is photoactivated as in Example III for three minutes. The solution was next removed from the slip. The slip was then placed into 1.5 ml of 1.0% Tween 20 in phosphate buffered saline and allowed to rotate on an orbital shaker. The wash solution was replaced every thirty minutes for 1.5 hours, and then allowed to continue washing for approximately 16 hours before they were exhaustively rinsed with PBS. The slips were evaluated using corneal endothelial cell tissue culture as in Example V, against control slips having adsorbed FP and untreated control slips. The adsorbed FP and control slips showed minimal cell outgrowth and the immobolized FP exhibited 28 times the outgrowth of the control slips.

While preferred embodiments of the invention have been described, it should be understood that various changes, adaptations and modifications may be made therein without departing from the spirit of the invention and the scope of the appended claims.

What is claimed is:

1. A method of providing a substrate having a solid surface, the method comprising the steps of:

(a) providing a polymer, (b) contacting the substrate surface with a composition comprising a plurality of molecules of the polymer, each having covalently bonded to it at least one latent reactive group capable of active specie generation in response to application of an external stimulus, under conditions which enable the polymer molecules to orient spatially so as to enable the latent reactive groups to come into covalent bonding proximity with the substrate surface; and (c) thereafter activating the latent reactive groups by application of the external stimulus to covalently bond the polymer molecules to the substrate surface.

2. A method according to claim 1 wherein the polymer comprises fibronectin.

3. A method according to claim 1 wherein the polymer comprises a cell attachment factor.

4. A method according to claim I wherein the substrate surface is polystyrene.

5. A method according to claim 1 wherein the substrate surface is silicone.

6. A method according to claim 1 wherein the external stimulus comprises actinic radiation.

7. A method according to claim 6 wherein the substrate surface is substantially free of functional groups added by pretreatment of the surface.

8. A method according to claim 6 wherein the polymer is a synthetic polymer.

9. A method according to claim 6 wherein the substrate surface is polystyrene.

10. A method according to claim 6 wherein the substrate surface is silicone.

11. A method of providing a substrate having a surface, the method comprising the steps of:
   (a) providing a polymer,
   (b) contacting the substrate surface with a composition comprising a plurality of molecules of the polymer, each having covalently bonded to it at least one latent reactive group selected from the group consisting of photoactivatable ketones under conditions which enable the polymer to orient spatially so as to enable the latent reactive groups to come into covalent bonding proximity with the substrate surface; and
   (c) thereafter activating the latent reactive groups by the application of the external stimulus to covalently bond the polymer molecules to the substrate surface.

12. A method according to claim 11 wherein the photoactivatable ketone is selected from the group consisting of benzophenones and acetophenones.

13. A method according to claim 12 where the photoactivatable ketone is benzophenone.

14. A method according to claim 11 wherein the method is used to modify the surface properties of a substrate having a solid surface, the method comprising the steps of:
   (a) providing a polymer having physical/chemical properties that are different than the physical/chemical properties of the substrate,
   (b) contacting the substrate surface with a composition comprising a plurality of molecules of the polymer, each having covalently bonded to it at least one latent reactive group selected from the group consisting of photoactivatable ketones under conditions which enable the polymer to orient spatially so as to enable the latent reactive groups to come into covalent bonding proximity with the substrate surface; and
   (c) thereafter activating the latent reactive groups by application of the external stimulus to covalently bond the polymer molecules to the substrate surface.

15. A method according to claim 14 wherein the polymer is used to modify the surface by providing it with a physical/chemical property selected from the group consisting of hydrophilic, hydrophobic, solvophilic, protein repulsion, antithrombogenic, and hemostatic properties.

16. A method according to claim 11 further comprising the step of covalently bonding one or more further monomers, oligomers or polymers to the polymer molecules covalently bound to the substrate surface.

17. A method according to claim 16 wherein further monomers or oligomers are covalently bound by polymerization to the surface-bound polymer molecules.

18. A method according to claim 16 wherein further polymers are covalently bound by grafting to the surface-bound polymer molecules.

19. A method according to claim 14 wherein the polymer is used to modify the surface by providing it with a physical/chemical property in the form of reactivity for covalent bonding of one or more further monomers, oligomers or polymers to the polymer molecules covalently bound to the substrate surface.

20. A method according to claim 19 further comprising the step of covalently bonding one or more monomers, oligomers or polymers to the polymer molecules covalently bound to the substrate surface.

21. A method according to claim 20 wherein one or more monomers or oligomers are covalently bound by polymerization to the surface-bound polymer molecules.

22. A method according to claim 20 wherein further polymers are covalently bound by grafting to the surface-bound polymer molecules.

* * * * *

UNITED STATES PATENT AND TRADEMARK OFFICE
CERTIFICATE OF CORRECTION

PATENT NO.  : 5,512,329
DATED       : Apr. 30, 1996
INVENTOR(S) : Patrick E. Guire, et al.

Page 1 of 2

It is certified that error appears in the above-indentified patent and that said Letters Patent is hereby corrected as shown below:

Item [57]

Abstract, line 6, replace "pretreatement" with --pretreatment--.
Column 1, line 13, replace "495" with --493--.
Column 8, line 51, replace "Introcular" with --Intraocular--.
Column 9, line 11, replace "azeotrophed" with --azeotroped--.
Column 9, line 45, replace "hyaluranic" with --hyaluronic--.
Column 10, line 3, replace "516/nm" with --516 nm--.
Column 10, line 5, replace "516/nm" with --516 nm--.
Column 10, line 45, replace "thimerasol" with --thimerosal--.
Column 10, line 56, replace "Pharmacueticals" with --Pharmaceuticals--.
Column 13, line 59, replace "poly methylmethacrylate" with --polymethylmethacrylate--.
Column 14, line 14, replace "(4-Benzoylbenzamido" with --(4-Benzoylbenzamido)--.
Column 15, line 15, replace "comparability" with --compatability--.

UNITED STATES PATENT AND TRADEMARK OFFICE
CERTIFICATE OF CORRECTION

PATENT NO. : 5,512,329
DATED : Apr. 30, 1996
INVENTOR(S) : Patrick E. Guire, et al.

It is certified that error appears in the above-indentified patent and that said Letters Patent is hereby corrected as shown below:

Column 16, line 14, replace "example" with --Example--.
Column 16, line 23, replace "slip" with --slip was--.
Column 16, line 36, replace "immobolized" with --immobilized--.

Signed and Sealed this

Twenty-fifth Day of February, 1997

BRUCE LEHMAN

Attest:

Attesting Officer

Commissioner of Patents and Trademarks